United States Patent [19]

Tanaka et al.

[11] Patent Number: 5,449,684
[45] Date of Patent: Sep. 12, 1995

[54] CYTOTOXIC COMPOUNDS

[75] Inventors: Jun-Ichi Tanaka; Tatsuo Higa, both of Okinawa, Japan; Khanit Suwanoborirux, Bangkok, Thailand; C. W. Jefford, Thoinex; G. Bernardinelli, Collex, both of CHX; Dolores G. Gravalos, Madrid, Spain

[73] Assignee: PharmaMar, S.A., Madrid, Spain

[21] Appl. No.: 191,336

[22] Filed: Feb. 3, 1994

[30] Foreign Application Priority Data

Feb. 3, 1993 [GB] United Kingdom ............... 9302044

[51] Int. Cl.$^6$ .................. A61K 31/335; C07D 309/00; C07C 69/74; C07C 62/00
[52] U.S. Cl. ........................... 514/452; 514/529; 514/572; 549/357; 560/118; 560/119; 560/126; 562/498; 562/500; 562/501; 562/508
[58] Field of Search ............... 549/357; 514/452, 572, 514/529; 560/118, 119, 126; 562/498, 501, 500, 508

[56] References Cited

U.S. PATENT DOCUMENTS 4,731,377 3/1988 Higa et al. .......................... 549/357
5,183,924 2/1993 Festal et al. ........................ 549/357

OTHER PUBLICATIONS

Manes et al., Tetrahedron Letters, vol. 25, No. 9, pp. 931–934 (1984).
Albericci et al., Tetrahedron, 38, 1881–1890 (1982).
Capon et al., Journal of Natural Products, vol. 50, No. 2, pp. 225–229 (1987).
Capon et al., J. Org. Chem., vol. 52, No. 3, (1987).
Hai-yin et al., J. Org. Chem., 56, 2112–2115 (1991).
Capon et al., Tetrahedron, vol. 41, No. 16, pp. 3391–3404 (1985).
Albericci et al., Tetrahedron Letters, No. 29, pp. 2687–2690 (1979).
Tanaka et al., J. Org. Chem., 58, 2999–3002 (1993).
Kashman et al., Tetrahedron Lett., 1707 (1979).

*Primary Examiner*—Cecilia Tsang
*Attorney, Agent, or Firm*—Ernest V. Linek

[57] ABSTRACT

Compounds isolated from a marine sponge, and derivatives thereof, have the formulae:

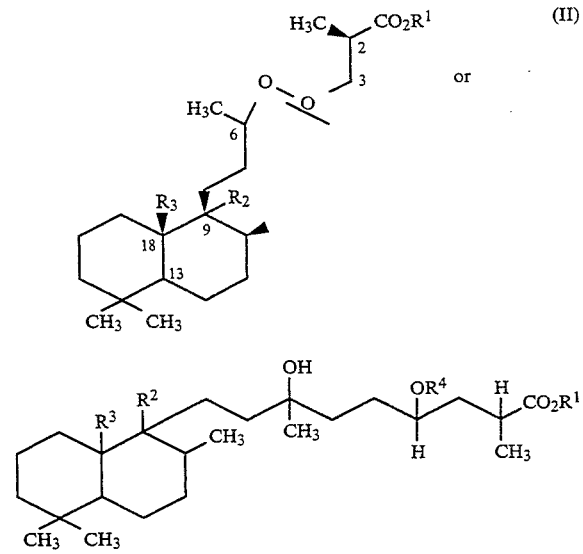

in which $R^1$ is H or lower alkyl; $R^2$ is OH or $CH_3$; $R^3$ is OH or $CH^3$, and $R^4$ H or MPTA. The compounds have antitumor and antiviral activity. The invention also provides pharmaceutical compositions containing the compounds and methods of treatment employing them.

18 Claims, No Drawings

CYTOTOXIC COMPOUNDS

This invention is concerned with cytotoxic compounds isolated from a marine sponge.

It has been found, in accordance with the present invention, that certain compounds which may be isolated from a Mycale sp sponge, and derivatives thereof, have cytotoxic activity.

According to the invention there are provided, as new compounds, 1,2-dioxane compounds of the formula:

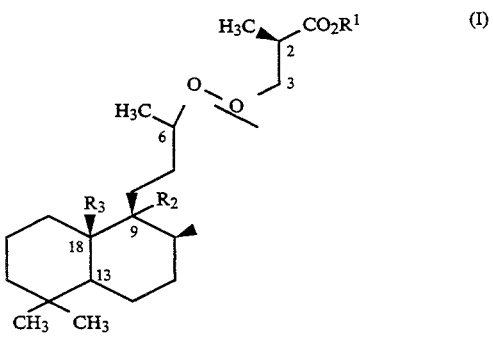

in which $R^1$ is a hydrogen atom or a methyl group and $R^2$ and $R^3$ are each a hydroxyl or methyl group. The invention further provides triols, obtainable from the above dioxane compounds (e.g. by hydrogenation) and having the formula:

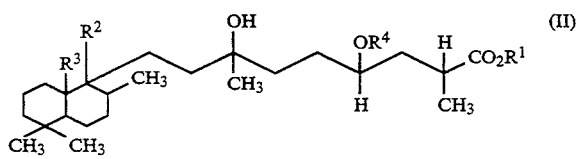

in which $R^1$, $R^2$ and $R^3$ have the meanings defined above, and $R^4$ is a hydrogen atom or MTPA group. The invention also provides compounds of formula (I) or (II) in the form of a pharmaceutically acceptable salts.

The compounds of formula (I) in which $R^1$ is hydrogen are obtained from a Mycale sp sponge. The Mycale sp. sponge was collected at a depth of 5 m around Kang Ta Shin off Sichang Island in Thai Bay. It was observed to inhabit a place having some currents. The color was light blue to grey. When collected, it gave off mucus and most of the sponge material dissolves leaving behind a fine tissue-like skeleton. In the water small sea cucumbers were observed residing on the surfaces of most of the sponge colony. It appears that the sea cucumbers were not eating the sponge but foreign matter on the surface.

Basically, the compounds may be isolated from the sponge by steeping in methanol, concentrating the extract and extracting with methylene chloride. The two compounds my be separated by gel chromatography and HPLC. The separated compounds may be subsequently esterified and/or hydrogenated to give compounds of formula (II). Compounds of formula (II) may later be transesterified.

As noted above, compounds in accordance with the invention have cytotoxic properties.

Therefore, the present invention also provides a method of treating any mammal affected by a malignant tumor sensitive to compounds above described, which comprises administering to the affected individual a therapeutically effective amount of these compounds or a pharmaceutically composition thereof; and a method of treating viral infections in mammals, comprising administering to a patient in need of such treatment, an antiviral effective amount of the compounds described in the present invention. In particular the compounds of the invention may be used in the treatment of mammalian lymphoma; human lung carcinoma and human colon carcinoma.

The present invention also relates to pharmaceutical preparations which contain as active ingredient these compounds, or a pharmaceutical acceptable acid addition salt thereof, as well as the process for its preparation.

Examples of pharmaceutical compositions include any solid (tablets, pills, capsules, granules, etc.) or liquid (solutions, suspensions or emulsions) suitable composition for oral, topical or parenteral administration, and they may contain the pure compound or in combination with any carrier or other pharmacologically active compounds. These compositions may need to be sterile when administered parenterally.

The correct dosage of a pharmaceutical composition of these compounds will vary according to the particular formulation, the mode of application and the particular situs, host and tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

In order that the invention may be well understood, the following Examples are given by way of illustration only.

EXAMPLE 1

Extraction and Isolation

The sponge as described above was extracted by steeping in mehanol (2×2.5 L) at room temperature. After concentration the residue was extracted with methylene chloride to give 3.38 of an oil. A portion (3.1 g) of the oil was chromatographed on silica gel (hexane/ethyl acetate). Fractions eluted with 10:1 to 3:1 hexane/ethyl acetate were further separated on ODS gel (methanol) and then by HPLC (ODS, MeOH/H₂O) to furnish 135 mg of mycaperoxide A [formula I, $R^1$=H; $R^2$=CH₃; $R^3$=OH] and 130 mg of mycaperoxide B [Formula I, $R^1$=H; $R^2$=OH; $R^3$=CH₃]. Structures of these compounds were determined by analysis of spectrocospic data by X-ray on Mycaperoxide A.

Mycaperoxide A

Colorless crystals. from acetone, mp 157°–159° C., $[\alpha]30_D$ −41.0 (c 1.28, acetone). IR (CHCl₃) 3520, 2950, 1710, 1460, and 1380 cm⁻¹. ¹H NMR (CDCl₃) ¢ 4.19 (1H, ddd, J=7.9, 7.9, 3.6 Hz), 2.75 (1, m), 1.21 (3H, s), 1.13 (3H, s), and 0.74 (3H, d, J=6.9 Hz). ¹³C NMR (CDCl₃)₃¢179.2 (s), 81.1 (d), 80.9 (s), 46.4 (d), 43.3 (s), 42.0 (d), 39.2 (d), 34.8 (t), 33.8 (s), 32.3 (t), 32.1 (q), 30.2 (q), 29.6 (t), 26.2 (t), 25.8 (t), 21.6 (t), 20.6 (q), 20.2 (t), 18.4 (t), 18.1 (q), 16.4 (q), 12.8 (q). EIMS m/z 410 (M+, 2), 395 (2), 281 (6), 111 (87), 95 (77), 69 (99), and 43 (100 rel %). HR EIMS m/z 410.3005 (−2.7 mmu for C₂₄H₄₂O₅).

Mycaperoxide B

Colorless oil, $[\tilde{a}]30_D$ −41.3° (c 1.27, acetone). IR (CHCl$_3$) 3520, 2950, 1715, 1465, and 1380 cm$^{-1}$. $^1$H NMR (CDCl$_3$) ¢ 4.20 (1H, m), 2.56 (1H, dq. J=7.2, 7.2 Hz), 1.36 (1H, dd, J=12.0, 2.4 Hz), 1.26 (3H, s). 1.12 (3H, d, J=7.2 Hz), 1.08 (1H, ddd, J=13.0, 13.0, 3.6 Hz), 0.87 (3H, s), 0.82 (3H, s), 0.80 (3H, d, J=6.7 Hz), and 0.78 (3H, s). $^{13}$C NMR (CDCl$_3$) 178.7 (s), 81.3 (d), 80.4 (s), 77.0 (s), 46.1 (d), 43.2 (s), 42.5 (d), 41.5 (t), 36.2 (d), 36.0 (t), 33.6 (q), 33.2 (s), 32.2 (t), 31.8 (t), 31.1 (t), 27.0 (t), 22.4 (t), 21.8 (q), 21.4 (t), 20.1 (q), 18.5 (t), 16.2 (q), 16.1 (q), and 12.5 (q). EIMS m/z 410 (M+, 11), 348 (8), 280 (4), 209 (42), 69 (100), and 43 (88 rel %). HR EIMS m/z 410.3042 (1 mmu for C$_{24}$H$_{42}$O$_5$).

EXAMPLE 2

Mycaperoxide A Methyl Ester

To a solution of 14.3 mg of mycaperoxide A in 1 ml of methanol was added drop by drop to a hexane solution of (trimethylsilyl) diazomethane (TMSCHN$_2$) until the red solution stayed yellow. After standing at room temperature for ten minutes, the solution was concentrated to give 14 mg (95%) of methyl ester as a gum; $[\tilde{a}]^{21}_D$+21°.

Methylation of mycaperoxide B in a similar manner gave the corresponding methyl ester as a gum; $[\alpha]_D^{21}$+8.9°.

EXAMPLE 3

A mixture of 13.8 mg of mycaperoxide A methyl ester, 5 mg of 10% Pd/C, and 4 ml of ethyl acetate was stirred under hydrogen overnight. The mixture was filtered and the filtrate concentrated to furnish a residue which was separated by preparative TLC (silica gel, 4:1 CH$_2$Cl$_2$/EtAOc) to give 4.0 mg (29%) of pure triol [Formula II, R$^1$=CH$_3$; R$^2$=CH$_3$; R$^3$=OH; R$^4$=H]; $[\alpha]^{20}_D$+9.6°.

Catalytic hydrogenation of 12.0 mg of mycaperoxide B methyl ester in a similar manner gave 9.9 mg (83%) of the corresponding triols [R$^1$=CH$_3$; R$^2$=OH; R$^3$=CH$_3$; R$^4$=H] as a gum, $[\alpha]_d^{20}$+14°.

EXAMPLE 4

Reaction of triol A with (+)-(R)-α-methoxy-α-trifluoromethyl) phenylacetyl (MTPA) chloride was effected by allowing a mixture of 1.5 mg of A, 15 ml of the MTPA chloride and 50 ml of pyridine to stand under nitrogen at room temperature for one hour. After consumption of the starting material was confirmed by TLC, a drop of water and two drops of methylene chloride and methanol were added. The mixture was then separated by preparative chromatography (silica gel, 5:1 methylene chloride/ethyl acetate) to give 1.25 mg (68%) of the (R)-MTPA ester as a gum, $[\alpha]_d^{22}$+23°. The similar treatment of triol A with (−)-(S) MTPA chloride in a similar manner gave 1.38 mg (65%) of the (S)-MTPA ester as a gum; $[\alpha]_D^{22}$−4.5°. A similar treatment of 1.5 mg of triol B with (R)-MTPA chloride gave the corresponding (R)-MTPA ester (1.25 mg) as a gum; $[\alpha]_D^{30}$30°. Similarly triol B gave 1.38 mg of the corresponding (S)-MTPA ester as a gum; $[\alpha]_D^{21}$+4.4°.

The antitumour activities of Mycaperoxide A and Mycaperoxide B have been determined "in vitro" in cell cultures of mouse leukemia P-388, human lung carcinoma A-549 and human colon carcinoma HT-29. The procedure was carried out using the method described by Raymond J. Bergeron et al. Biochem Bioph. Res. Comm. 1984, 121(3), 848–854 and by Alan C Shroeder et al. J. Med. Chem. 1981, 24 1078–1083.

Antitumor activity:

| COMPOUND | IC50 (μ/ml) | | |
|---|---|---|---|
| | P-388 | A-549 | HT-29 |
| Mycaperoxide A | 0.5 | 0.5 | 0.5 |
| Mycaperoxide B | 1.0 | 1.0 | 1.0 |

The antiviral activities of these compounds have also been determinated "in vitro" against HSV (Herpes simplex virus) and VSV (Vesicular stomatitis virus). The methodology used to carry out this determination is described by Raymond J. Bergeron et.al. Biochem. Bioph. Res. Comm. 1984, 121(3), 848–854 and by Alan C. Shroeder et al. J. Med. Chem. 1981, 24 1078–1083.

The following results were obtained.

Antiviral activity:

| COMPOUND | IC50 (μg/ml) | |
|---|---|---|
| | HSV | VSV |
| Mycaperoxide A | >1 | 2 |
| Mycaperoxide B | >1 | 4 |

We claim:

1. A compound having the formula I:

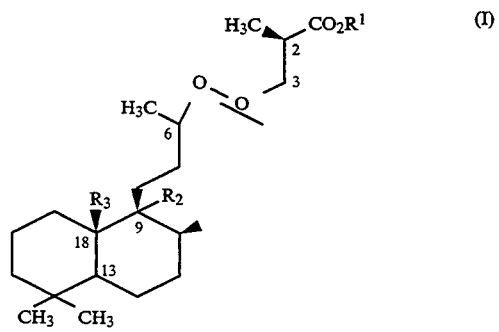

wherein R$^1$ is H or lower alkyl, R$^2$ is OH or CH$_3$ and R$^3$ is OH or CH$_3$; or a pharmaceutically acceptable salt thereof.

2. The compound of claim 1, wherein R$^1$ is methyl.

3. A compound having the formula II:

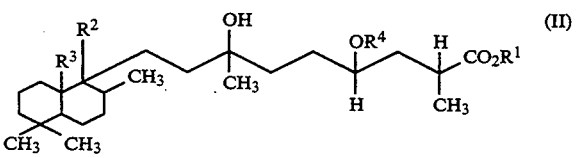

wherein R$^1$ is H or a lower alkyl, R$^2$ is OH or CH$_3$, R$^3$ is OH or CH$_3$ and R$^4$ is H or α-methoxy-α-(trifluoromethyl)phenylacetyl; or a pharmaceutically acceptable salt thereof.

4. The compound of claim 3, wherein R$^1$ is methyl.

5. The substantially pure compound mycaperoxide A, having the following chemical structure:

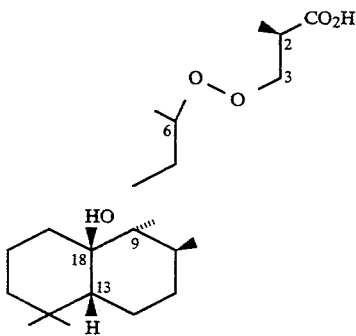

6. The substantially pure compound mycaperoxide B, having the following chemical structure:

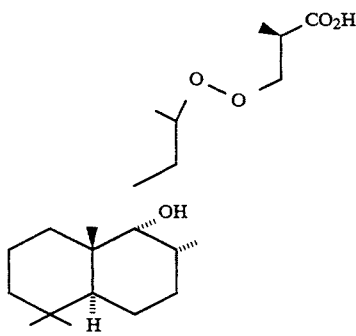

7. A pharmaceutical composition comprising a compound of claim 1 in association with a pharmaceutical carrier or diluent.

8. A pharmaceutical composition comprising a compound of claim 3 in association with a pharmaceutical carrier or diluent.

9. A pharmaceutical composition comprising a compound of claim 5 in association with a pharmaceutical carrier or diluent.

10. A pharmaceutical composition comprising a compound of claim 6 in association with a pharmaceutical carrier or diluent.

11. A method of inhibiting the growth of mammalian tumors selected from the group consisting of leukemia, lung carcinoma and colon carcinoma, comprising administering to a subject in need of such treatment, an effective antitumor amount of a compound of claim 1.

12. A method of inhibiting the growth of mammalian tumors selected from the group consisting of leukemia, lung carcinoma and colon carcinoma, comprising administering to a subject in need of such treatment, an effective antitumor amount of a compound of claim 3.

13. A method of inhibiting the growth of mammalian tumors selected from the group consisting of leukemia, lung carcinoma and colon carcinoma, comprising administering to a subject in need of such treatment, an effective antitumor amount of a compound of claim 5.

14. A method of inhibiting the growth of mammalian tumors selected from the group consisting of leukemia, lung carcinoma and colon carcinoma, comprising administering to a subject in need of such treatment, an effective antitumor amount of a compound of claim 6.

15. A method of inhibiting the growth of mammalian viruses selected from the group consisting of herpes simplex virus and vesicular stomatitis virus comprising administering to a subject in need of such treatment, an effective antiviral amount of a compound of claim 1.

16. A method of inhibiting the growth of mammalian viruses selected from the group consisting of herpes simplex virus and vesicular stomatitis virus comprising administering to a subject in need of such treatment, an effective antiviral amount of a compound of claim 3.

17. A method of inhibiting the growth of mammalian viruses selected from the group consisting of herpes simplex virus and vesicular stomatitis virus comprising administering to a subject in need of such treatment, an effective antiviral amount of a compound of claim 5.

18. A method of inhibiting the growth of mammalian viruses selected from the group consisting of herpes simplex virus and vesicular stomatitis virus comprising administering to a subject in need of such treatment, an effective antiviral amount of a compound of claim 6.

* * * * *

UNITED STATES PATENT AND TRADEMARK OFFICE
CERTIFICATE OF CORRECTION

PATENT NO. : 5,449,684
DATED : September 12, 1995
INVENTOR(S) : Tanaka et al.

It is certified that error appears in the above-indentified patent and that said Letters Patent is hereby corrected as shown below:

On the Cover page, item [57], in the ABSTRACT, please replace the first formula with the following formula:

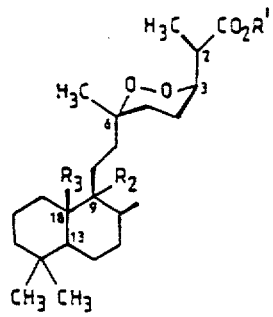

column 1, please replace the first formula with the following formula:

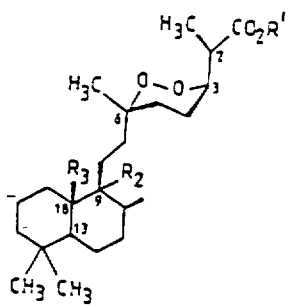

UNITED STATES PATENT AND TRADEMARK OFFICE
CERTIFICATE OF CORRECTION

PATENT NO. : 5,449,684
DATED : September 12, 1995
INVENTOR(S) : Tanaka et al.

It is certified that error appears in the above-indentified patent and that said Letters Patent is hereby corrected as shown below:

column 4, claim 1, please replace the formula (I) with the following formula:

--
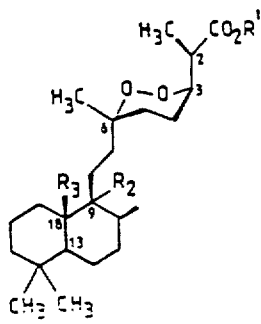
-- column 5, claim 5, please replace the formula with the following formula:

--
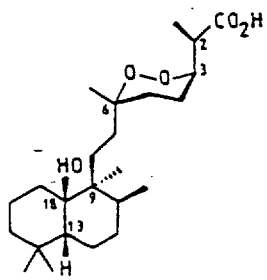
--

UNITED STATES PATENT AND TRADEMARK OFFICE
CERTIFICATE OF CORRECTION

PATENT NO. : 5,449,684
DATED : September 12, 1995
INVENTOR(S) : Tanaka et al.

It is certified that error appears in the above-indentified patent and that said Letters Patent is hereby corrected as shown below:

column 5, claim 6, please replace the formula with the following formula:

--

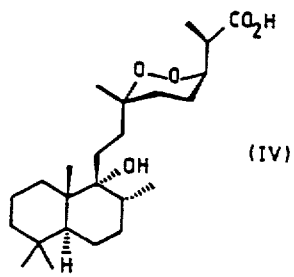

(IV)

--

Signed and Sealed this

Twenty-seventh Day of February, 1996

Attest:

BRUCE LEHMAN

Attesting Officer    Commissioner of Patents and Trademarks